United States Patent
Scofield et al.

(10) Patent No.: US 6,553,849 B1
(45) Date of Patent: Apr. 29, 2003

(54) ELECTRODYNAMIC PARTICLE SIZE ANALYZER

(76) Inventors: Dillon F. Scofield, 128 Country Flower Dr., Newark, DE (US) 19711; Vitaly V. Romanenko, Karpinskogo Street 38-2-41, St. Petersburg, 195252 (RU)

( * ) Notice: Subject to any disclaimer, the term of this patent is extended or adjusted under 35 U.S.C. 154(b) by 0 days.

(21) Appl. No.: 09/830,394

(22) PCT Filed: Oct. 22, 1999

(86) PCT No.: PCT/US99/24882

§ 371 (c)(1),
(2), (4) Date: Apr. 26, 2001

(87) PCT Pub. No.: WO00/25109

PCT Pub. Date: May 4, 2000

Related U.S. Application Data

(60) Provisional application No. 60/106,015, filed on Oct. 28, 1998.

(51) Int. Cl.$^7$ ............................................. G01N 15/02
(52) U.S. Cl. ..................... 73/865.5; 324/71.1; 356/336; 702/29
(58) Field of Search .................... 73/865.5; 356/335, 356/336; 324/71.4; 702/29

(56) References Cited

U.S. PATENT DOCUMENTS

| | | | | |
|---|---|---|---|---|
| 2,825,872 A | | 3/1958 | Stubbs et al. | 73/865.5 X |
| 2,986,923 A | * | 6/1961 | Vonnegut | 73/28.02 |
| 3,208,286 A | | 9/1965 | Richard | 73/865.5 |
| 3,413,545 A | * | 11/1968 | Whitby | 324/71.1 |
| 3,718,029 A | | 2/1973 | Gourdine et al. | 73/28.02 |
| 3,740,149 A | * | 6/1973 | Whetten | 356/335 |
| 3,740,553 A | * | 6/1973 | Whetten | 250/292 |
| 3,763,428 A | * | 10/1973 | Preist | 73/865.5 X |

(List continued on next page.)

FOREIGN PATENT DOCUMENTS

| | | | | |
|---|---|---|---|---|
| EP | 432752 A2 | * | 6/1991 | G03G/13/09 |
| EP | 0 465 205 | | 1/1992 | G01N/15/02 |
| EP | 0 562 630 | | 9/1993 | G01N/15/02 |

(List continued on next page.)

OTHER PUBLICATIONS

TDB–Acc–No.: NN82014159 "Analysis of Toner Size and Charge Distribution" *IBM TEchnical Disclosure Bulletin* vol. 24, No. 8, pp. 4159–4160, Jan. 1982.*

Derwent–Acc–No.: 1984–125614 abstract of SU 1035477A Aerosol Particle size distribution determn.–by impact charging of aerosol stream particles and measurement of their electic mobility (Mirme et al), Aug. 1983.*

(List continued on next page.)

*Primary Examiner*—Thomas P. Noland
(74) *Attorney, Agent, or Firm*—RatnerPrestia

(57) ABSTRACT

An apparatus and method for determining the particle size distribution of a plurality of particles in a sample, the apparatus comprising a particle charging chamber for charging the particles in proportion to a dimension of the particle, such as surface area, and from which charged particles exit primarily one-at-a-time, a collector electrode for catching the exiting particles, and a charge-measuring device that produces an output with a value representing the measured particle charge. The particle charging chamber may comprise a number of electrodes and a DC voltage source connected to the electrodes. A conversion device, such as a computer, may receive the output from the charge-measuring device and convert measured individual particle charge data to a particle surface area distribution. The apparatus may further comprise light beams and light detecting means between the exit of the charging chamber and the collector electrode, for determining particle terminal velocity as it exits the charging chamber. A method for measuring particle size using the apparatus described herein is also disclosed.

37 Claims, 5 Drawing Sheets

U.S. PATENT DOCUMENTS

| | | | |
|---|---|---|---|
| 3,801,869 A | | 4/1974 | Masuda .................. 361/227 |
| 3,853,750 A | | 12/1974 | Volsy .................. 209/127.1 |
| 4,375,673 A | * | 3/1983 | Lewis et al. .................. 702/29 |
| 4,534,856 A | | 8/1985 | Weiss et al. .................. 209/1 |
| 4,633,714 A | * | 1/1987 | Mazumder et al. .... 73/865.5 X |
| 4,854,705 A | | 8/1989 | Bachalo .................. 356/336 |
| 4,906,094 A | | 3/1990 | Ashida .................. 356/336 |
| 4,984,889 A | | 1/1991 | Sommer .................. 356/336 |
| 5,030,843 A | | 7/1991 | Wakamura .................. 250/574 |
| 5,033,851 A | | 7/1991 | Sommer .................. 356/338 |
| 5,135,306 A | | 8/1992 | Kanebako et al. .......... 356/336 |
| 5,214,386 A | * | 5/1993 | Singer et al. .......... 324/71.1 X |
| 5,245,290 A | * | 9/1993 | Connon et al. ........ 73/865.5 X |
| 5,257,087 A | | 10/1993 | Furuya .................. 356/336 |
| 5,266,900 A | * | 11/1993 | Eppins .................. 324/452 |
| 5,298,967 A | | 3/1994 | Wells .................. 356/336 |
| 5,305,072 A | | 4/1994 | Sawada et al. ............ 356/336 |
| 5,416,580 A | | 5/1995 | Trainer .................. 356/336 |
| 5,616,872 A | * | 4/1997 | O'Brien .................. 73/865.5 |
| 5,939,649 A | | 8/1999 | Boulaud et al. .......... 73/865.5 |
| 6,012,343 A | * | 1/2000 | Boulaud et al. .......... 73/865.5 |
| 6,281,972 B1 | * | 8/2001 | Ebara et al. .............. 356/336 |

FOREIGN PATENT DOCUMENTS

| | | | | |
|---|---|---|---|---|
| EP | 716350 A2 | * | 6/1996 | ............ G03G/9/08 |
| EP | 725317 A1 | * | 8/1996 | ............ G03G/9/08 |
| EP | 327548 B1 | * | 12/1996 | .......... G01N/15/02 |
| JP | 61-281975 | * | 12/1986 | .................. 324/72 |
| JP | 1-126568 | * | 5/1989 | .................. 324/72 |
| JP | 2-145940 | * | 6/1990 | .................. 250/550 |
| JP | 04369462 | | 12/1992 | .................. 250/573 |
| JP | 05206235 | | 8/1993 | .................. 356/336 |
| RU | 1438838 | | 11/1988 | |
| RU | 1447408 | | 12/1988 | |
| RU | 1475717 | | 4/1989 | |
| RU | 1487995 | | 6/1989 | |
| RU | 1519776 | | 11/1989 | |
| RU | 1558483 | | 4/1990 | |
| RU | 1563762 | | 5/1990 | |
| RU | 1651961 | | 5/1991 | |
| RU | 1736611 | | 5/1992 | |
| RU | 1754213 | | 8/1992 | |
| RU | 1764699 | | 9/1992 | |
| RU | 1773487 | | 11/1992 | |
| RU | 1773488 | | 11/1992 | |

OTHER PUBLICATIONS

Derwent–Acc–No.: 1991–308718 abstract of SU 1608499 A Measuring dispersed composition of coursely dispersed aerosol–passing charged particles through variable and constant electric fields (Kolobashki et al), Nov. 1990.*

International Search Report dated Oct. 22, 1999 to Application No. PCT/US99/24882 (corresponding PCT application) Published in WO 00/25109 in May 2000.

* cited by examiner $E = 0.005 \times 10^6$

ELECTRODYNAMIC PARTICLE SIZE ANALYZER

This application claims priority to International Application No. PCT/US99/24882, filed on Oct. 22, 1999, and to Provisional U.S. Application No. 60/106,015, filed on Oct. 28, 1998.

TECHNICAL FIELD

This invention relates to a particle size analyzer and more particularly to an apparatus and method for determining the particle size distribution in dry powders by charging the particles and measuring the individual charge accumulated on each particle in a sample.

BACKGROUND OF THE INVENTION

Characterizing particles that make up bulk materials has become increasingly important as the sophistication and control requirements of industrial processes increase. In the past the usual method was to use a microscope and measure the size distribution of an exemplary sample of the material to obtain an indication of the mean particle size and size distribution.

More recently a number of instruments have been developed to avoid the tedious and labor intensive process of measuring and counting particles under the microscope, by apparatus which can provide a particle size measurement and particle size distribution analysis automatically.

The range of particle size measured, particularly of dry powders, typically has a mean diameter between 1 $\mu$m and 10 $\mu$m. In most instances the instruments used employ indirect measurement techniques which include sieve fractionation, laser light scattering, dynamic light scattering, sedimentation/centrifugation, and gas absorption.

More recently, in an article published in the Proceedings of the 7th International Metrology Congress, Oct. 17–19, 1995, Niemes, France, pp. 215–217, entitled "An Electrodynamic Method Of Obtaining Calibration Materials For Granulometry", authored by V. J. Gerasimov and V. V. Romanenko, and incorporated herein by reference, it was shown that it is possible to obtain narrow-disperse calibration powders by using electrodynamic sedimentation of powders. In this article it is proposed that dry powder may be divided by particle size by subjecting the powder to a charging DC voltage applied between two inclined angled electrodes and providing a number of openings along a bottom electrode and an ancillary air stream of controlled velocity. By controlling the inclination of the bottom electrode, particles are separated along the electrode by mass and can be collected at specific points to obtain particles of selected similar mean diameter.

Most of the above systems, except for systems relying on the size measurement of the actual particle under a microscope, typically segregate a number of particles and calculate an average diameter for the segregated particles. Others use a means of fitting a presumed particle size distribution to a size sensitive response such as in the laser light scattering methods.

SUMMARY OF THE INVENTION

The present invention provides an instrument for automatically charging and obtaining a direct measurement of a dry powder's particle charge distribution in a sample, which uses electrodynamic particle separation in a new way in combination with an electrometer to obtain a measurement of the individual, particle-by-particle, charge on a plurality of charged particles, and to present an analysis of the charge distribution. The charge on each particle is related to the particle surface area and thus is also an indirect indication of the particle equivalent sphere or cube diameter. This process has the advantage that individual particles are measured and the individual particle distribution is obtained, rather than providing an average particle area or volume measure or a fit to a response function indirectly reflecting the particle size distribution.

In accordance with the present invention, there is provided an apparatus for determining the particle size distribution of a plurality of particles in a sample, the apparatus comprising a particle charging chamber adapted to charge the particles to a saturation level proportional to a dimension of the particle and to release particles from the charging chamber primarily one-at-a-time, a collector electrode located outside the charging chamber, and a charge-measuring device connected to the collector electrode for producing an output with a value representing the measured charge. The particle charging chamber may also be a pseudo-fluidization chamber such as, for example, an electrodynamic pseudo-fluidization chamber. Such a particle charging chamber comprises a top and a bottom electrode therein, a DC voltage source connected to the top and bottom electrodes, and a conversion device for receiving the output from the charge-measuring device and for converting measured individual particle charge data to a particle surface area distribution. The bottom electrode inside the particle charging chamber is spaced from the top electrode and has an exit orifice, an inner surface facing the top electrode, and an outer surface opposite the inner surface. The particle charging chamber further comprises a side wall extending between the top and bottom electrodes and a means for inserting the plurality of particles in the chamber. The collector electrode is aligned with the bottom electrode exit orifice and is spaced therefrom. The DC voltage source applies a voltage to the top and bottom electrodes of a magnitude insufficient to cause arcing between the electrodes.

The apparatus may further include an enclosure defining a space enclosing the particle charging chamber and collector electrode. This space may contain a gas, in particular an inert gas such as nitrogen, at a pressure above atmospheric pressure.

The chamber may be subdivided into subchambers by a plurality of middle electrodes located between the top and bottom electrodes and spaced therefrom, for example a single middle electrode may divide the chamber into an upper section and a lower section.

Such a middle electrode may have a convex surface with an apex facing the top electrode. The orifice in the middle electrode is placed away from the apex of the convex surface. The DC voltage source may apply a first DC voltage between the middle electrode and the bottom electrode and a second DC voltage between the top and middle electrodes, the DC voltages insufficient to produce arcing between the electrodes.

The apparatus may further include one or more fan-shaped light beams, such as two beams in parallel spaced planes between the exit orifice and the collector electrode, and a means for detecting any beam disruption by the passage of a charged particle and for generating an electrical signal indicating the passage and time of passage of any such particle through each of the beams of light.

In accordance with the apparatus of the present invention, there is also provided a method for determining a particle size distribution of a plurality of particles having a plurality of sizes by charging the plurality of particles and measuring a charge magnitude for each particle. The method comprises the steps of charging each of the particles in a particle charging chamber to a saturation level proportional to a dimension of the particle and releasing the particles from the chamber primarily one at a time. For example, the particles may be introduced in a space between a pair of electrodes in the presence of a static electric field wherein the method further includes providing an orifice in one of the pair of electrodes. The method also comprises collecting any charged particles exiting the particle charging chamber, such as through the orifice, and generating an electrical signal having a magnitude indicative of the charge of any such escaping charged particle; and using the distribution of the electrical signal magnitudes of a plurality of charged particles as an indicator of the particle surface area distribution.

BRIEF DESCRIPTION OF THE DRAWING

The following drawing will be used to illustrate this invention and are provided herein for the purposes of facilitating the explanation of the way the apparatus of this invention operates.

DETAILED DESCRIPTION OF THE INVENTION

The invention will next be described with reference to the figures wherein same numbers indicate same features.

Figure 1A:
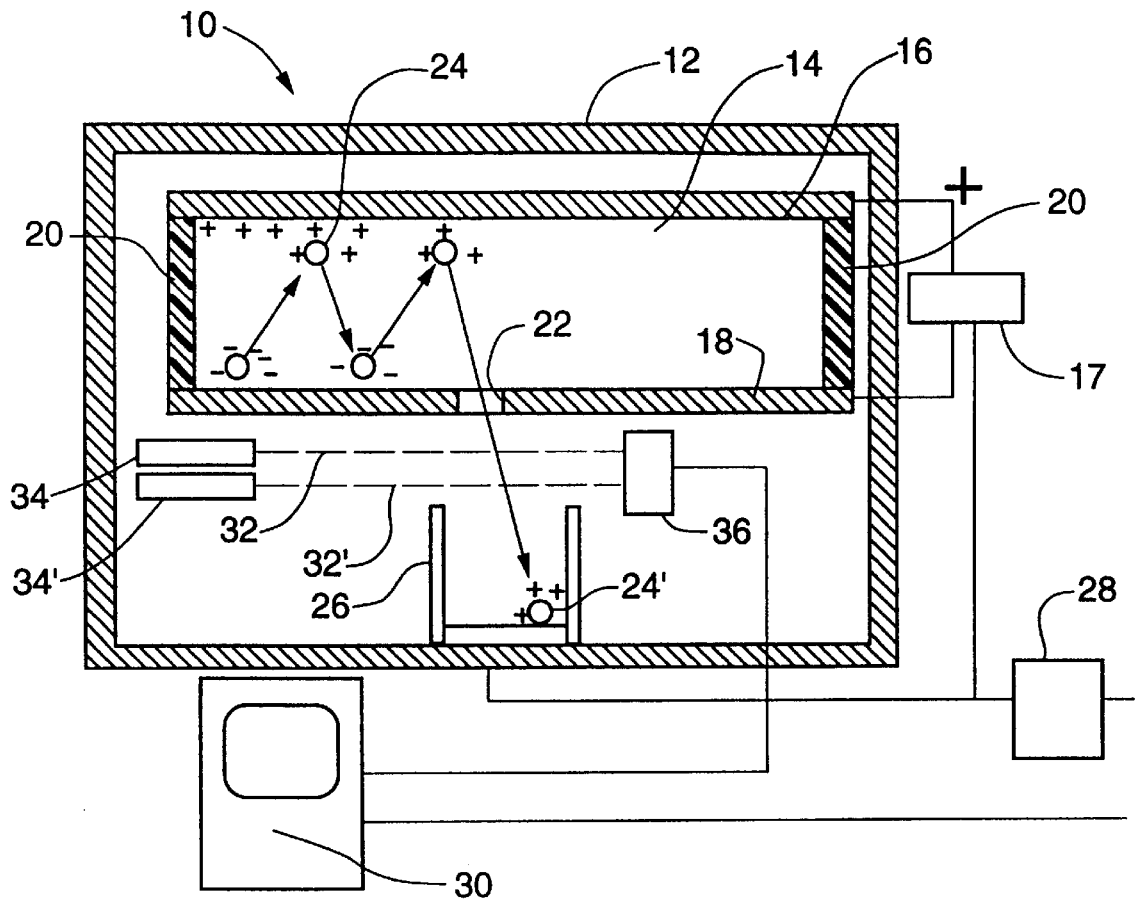
FIG. 1A is a schematic illustration of an apparatus in accordance with the present invention.

Referring now to FIG. 1A, there is illustrated an electrodynamic particle size analyzer 10 according to the present invention. In its most elementary form, the apparatus comprises an enclosure 12 within which is located a particle charging chamber 14 bounded by a top electrode 16, a bottom electrode 18, and insulating side walls 20. Bottom electrode 18 includes an orifice 22. Adjacent and below this orifice is placed a collector electrode 26.

A power supply 17 is connected between the top and bottom electrodes and applies a high DC voltage to the electrodes. As illustrated the DC source is connected so that the top electrode voltage is at a positive voltage and the bottom electrode is at a negative voltage. (The applied voltage can be reversed in an alternate embodiment, however, without effecting the operation of this invention.)

As explained in the aforementioned article by V. I. Gerasimov and V. V. Romanenko incorporated herein by reference, particles introduced in the charging chamber in contact with the bottom electrode accumulate a charge as a result of this contact, and under the influence of the applied field are repelled from the lower electrode and attracted to the top electrode, where they again accumulate a new charge of opposite polarity then are repelled from the top electrode and attracted to the bottom electrode.

The result of this effect is the formation of a stable suspension (cold plasma) of particles 24 that oscillate between electrodes. As the particles oscillate, occasionally particles escape from the chamber through the orifice 22 and impinge on the collector electrode 26 which is placed adjacent to the orifice and aligned so as to receive escaping particles. Thus, orifice 22 is sized so as to permit escape of particles primarily one at a time. Collector electrode 26 is preferably shaped as a hollow cylinder having an open top and a closed bottom. The charge of each such particle 24' that hits the collector electrode is measured using a charge-measuring amplifier and related electronics 28.

The surface charge Q is proportional to the convex outside surface area of the particle with a proportionality constant characteristic of the applied field strength and dielectric constants. The speed of a particle exiting the orifice is proportional to the charge, the accelerating field between the electrodes, i.e., the Lorentz (electrostatic) force, and inertial and gravitational forces on the particle.

Measurement of the charge by integration of the current pulse produced as each particle impinges on a collector electrode provides a particle-by-particle estimate of the particle surface area size using the equation:

$$Q = (2/3)\pi^3 \epsilon \epsilon_o E R^2 \qquad (1)$$

where: Q=charge on the particle, $\epsilon$=relative permitivity of the ambient medium, $\epsilon_o$=permitivity of vacuum, E=electric field strength in charging chamber before exit, R=radius of sphere, and solving for the sphere radius. The surface area of an equivalent sphere may then be calculated using surface area= $\sigma 4\pi R^2$, where $\sigma$ is a shape factor experimentally determined using calibration samples and is used to account for anomalies in surface area related to the specific particulate material being measured. Instrument calibration involves using a sample of spherical particles of verified mean radius, then introducing a scaling factor ($\sigma$) so the measured results agree with the known results. It is implicit in Equation 1 that the charge on the particle depends on the surface area of the particle and the electric field intensity, where the electric field intensity is defined as the potential difference between the electrodes divided by the distance between them.

The area size distribution can then be displayed, for example by using a histogram of the individual current pulses, or a multi-channel analyzer. Other presentations of the data may also be used. The histogram provides a quantitative indication of the charge distribution that is translated to the particle surface area distribution for the particles in a particular sample. The histogram may be displayed on a computer display 30, such as the one shown in FIG. 1A. Various particle size distribution parameters may also be conventionally computed and displayed accompanying the distribution.

Figure 1B:
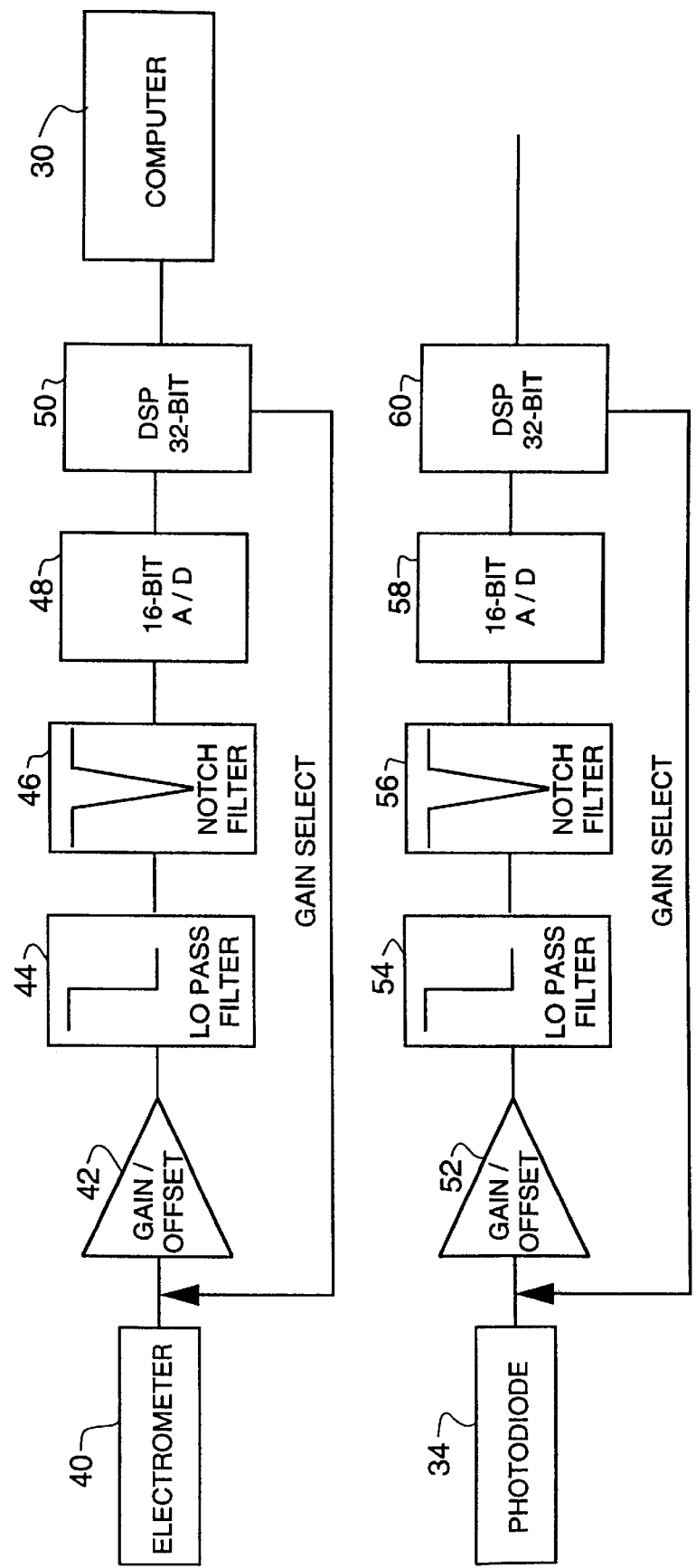
FIG. 1B shows a simplified diagram of the electronic signal detection circuit used to detect the particle charges and the light beam disruption signals.

Referring now to FIG. 1B, there is shown the typical elements comprising the charge detection electronics in an exemplary embodiment.

An electrometer 40 is used to detect the charge of a particle 24' contacting the collector electrode 26. The electrometer output is amplified in amplifier 42, filtered through a low pass filter 44 and a notch filter 46 (60 Hz for the United States, 50 Hz for other countries). It is then digitized, preferably in a 16-bit analog-to-digital (A/D) converter 48. The signal is further processed, preferably, in signal processor 50, which may be a 32-bit digital signal processor (but may also be a general purpose computer) and entered into computer 30.

Computer 30 then converts the processed electrometer output, which is indicative of the measured particle charge, to a particle surface area measurement using Equation 1 and accumulates such measurements to provide a particle surface area distribution. A computer is only one type of conversion device that may be used for converting the measured charges to a surface area distribution, and any known such analog or digital device may be used. For example, an exemplary analog system may comprise an analog pulse detector/integrator that front ends a boxcar integrator or multichannel analyzer.

The representation of the electronic components in this embodiment is given only schematically because there are numerous ways in which a charge signal may be detected, measured and amplified for further analysis and display. Such signal processing techniques are well known in this art and no particular circuit for achieving signal detection is considered as particularly advantageous provided that it is capable of detecting charges of very small magnitude. However, a vacuum tube electrometer may be preferable to an electrometer having solid state electronics, as solid state electronics are more likely to be destroyed in the unlikely event an arc is created. Where such a vacuum tube electrometer is used, the particle preferably has a negative charge when it hits the collector electrode 26, and thus top electrode 16 is also negative.

Returning now to FIG. 1A there is also shown a light source 36 which generates a plurality of two sheet light beams 32 and 32' extending in parallel planes below the orifice positioned to intercept the exiting particles.

Detector 34 detects focused scattered light resulting from a particle passing through a light sheet, and it produces a signal indicative of this disruption. Two sequential signals are produced separated in time by the time interval it takes a particle to transit the distance between the two beams. The velocity of the particle can thus be accurately determined given a known distance between the light sheets, using a timer to measure the time interval. More than two light beams may be used to obtain a more accurate measurement of the particle velocity as it exits the orifice, and its terminal velocity as it travels toward the collector plate. Particularly advantageous are customized diffraction grating generating multiple parallel sheets of light. In an alternate embodiment, only a single light sheet may be used, wherein the time-of-flight of the particle is computed between the signal produced when the particle passes through the single light sheet and a signal produced when the particle hits an essentially flat or slightly curved concave upward collector electrode.

As shown in FIG. 1B, the signal from the light detector is also processed through an amplifier 52, then filtered through a low pass filter 54 and a notch filter 56 (60 Hz for the United States, 50 Hz for other countries). It is then digitized, preferably in a 16-bit analog to digital converter (A/D) 58. The signal is further processed in digital signal processor 60, which again can be a 32-bit processor, and also entered into computer 30. The charge signal and velocity information for each particle are stored in association with each other so that both the velocity and the charge information associated with a particle may be retrieved for further processing at any time.

The combined velocity and charge signals may be used to calculate the particle mass. Given the measure of the particle-by-particle charge and the known applied electric field, the measurement of the particle terminal velocity allows an estimate of the particle-by-particle mass using:

$$V_L = \pi \varepsilon \varepsilon_0 E^2 R / (9\eta) = \frac{QE}{6\pi\eta R} \quad (2)$$

$$m_p = \rho V = \rho \frac{4\pi}{3} R^3 \quad (3)$$

$$m_p = \rho \frac{4\pi}{3} \left( \frac{QE}{6\pi\eta V_L} \right)^3$$

where $\rho$ is the known density of the particles and the volume V is calculated using an equivalent sphere approximation for the shape of the particle. The measured charge Q is known from the integration of the electrometer current pulse. E is the applied field in the free flight region. $V_L$ is the (Stokes) terminal velocity in the electric field of the free flight region shortly after the particle exits the orifice. $\eta$ is the absolute viscosity of the ambient gas (e.g., nitrogen). Because the shape (sphericity) of the particle and associated drag can influence terminal velocity, the accuracy of calculated mass based on terminal velocity is also affected by particle sphericity.

Figure 2:
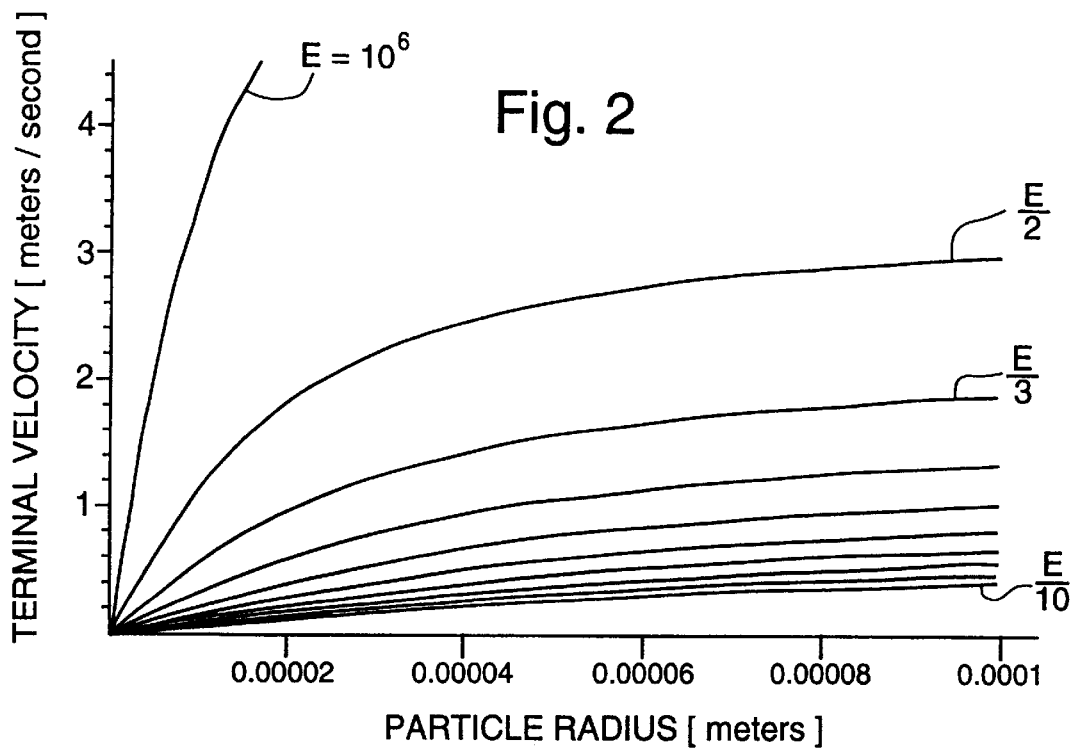
FIG. 2 shows a family of curves of particle terminal velocity as a function of particle radius at varying field strengths.

Referring now to FIG. 2, there is shown a family of curves derived from equation 2 for a given $\eta$ and a measured Q, showing Stokes velocity $V_L$ versus particle radius for various field strengths E. This family of curves shows that the field can be adjusted for increased sensitivity for larger or smaller particles.

Figure 5:
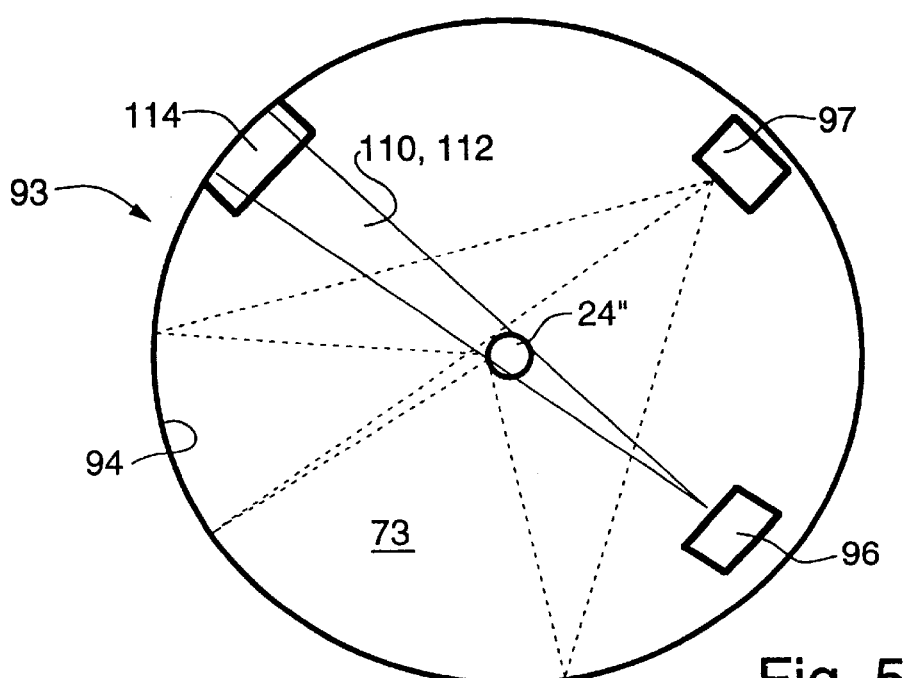
FIG. 5 shows a top view of the light beams for detecting the passage of a charged particle.
Figure 3:
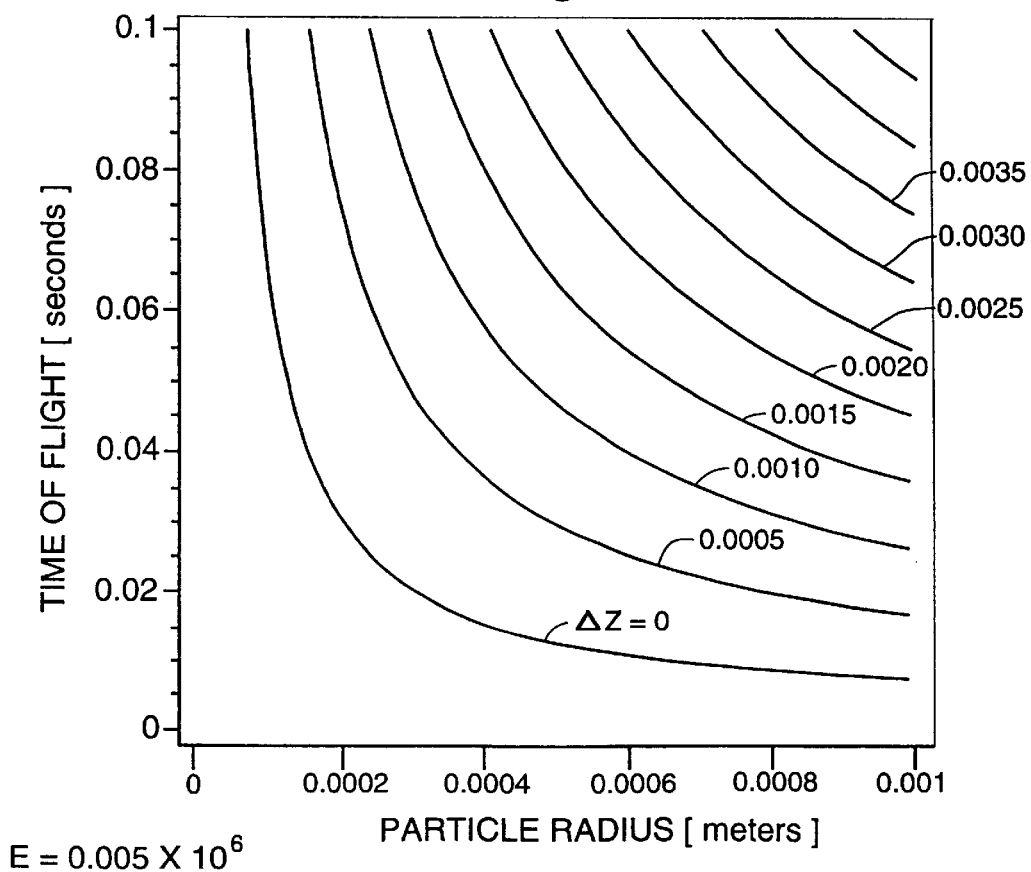
FIG. 3 shows a family of curves showing particle time of flight as a function of particle radius at varying free flight region gap distance.

Referring now to FIG. 3, there is shown a family of curves, also derived from equation 2 for a given $\eta$, a measured Q, and a constant $E=0.05\times10^6$ V/m, showing the particle time of flight versus radius for various distances $\Delta z$ in meters between electrodes. Thus, FIG. 5 shows the effect of varying the gap in the free flight region on the particle time of flight for particles of varying radii. Deviations from the family of curves specific to the conditions under which the instrument of the present invention is used, indicate anomalous shape dependency.

Figure 4A:
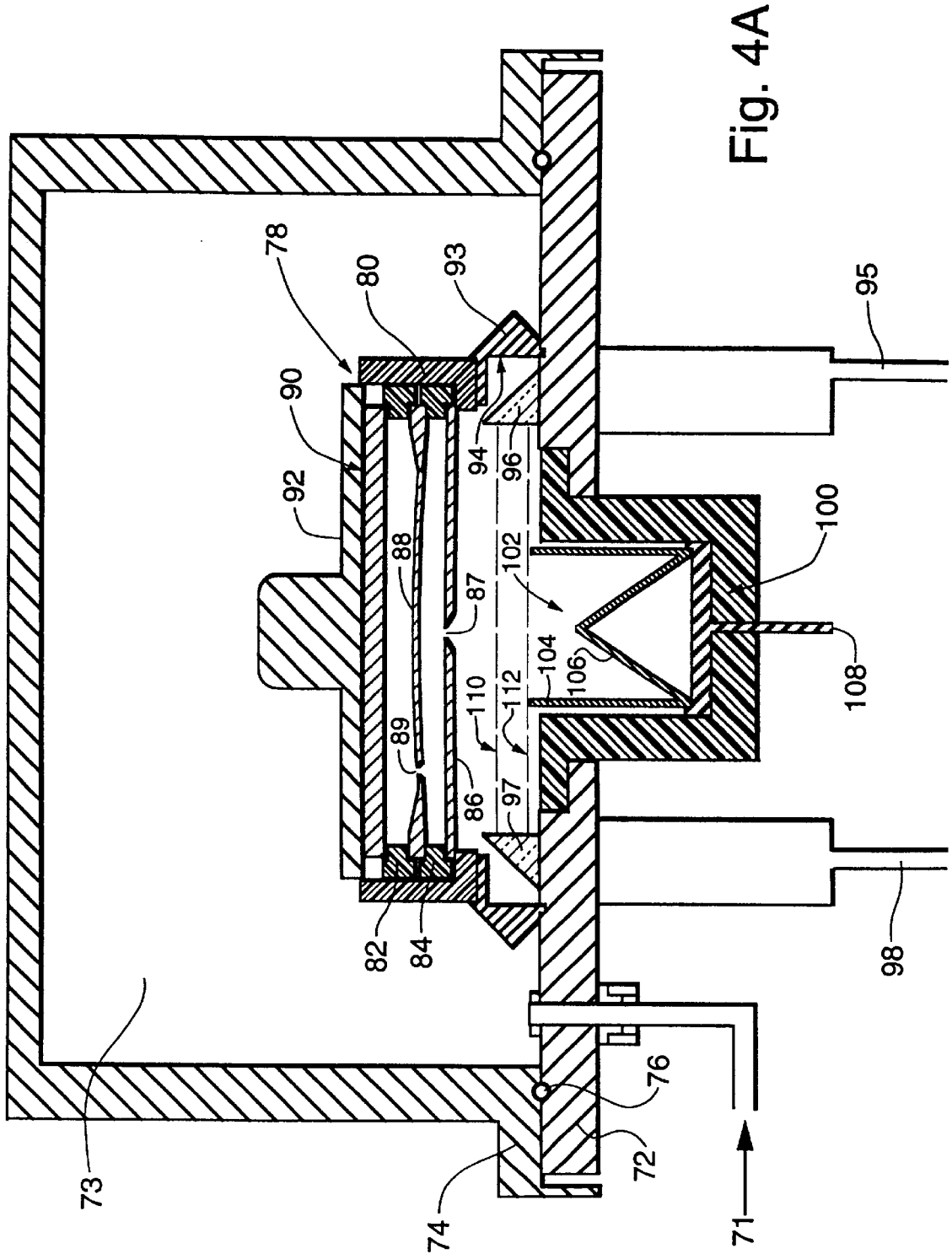
FIG. 4A is a schematic illustration of an alternate embodiment of an apparatus according to the present invention.

Referring now to FIG. 4A, there is shown a preferred embodiment of the electrodynamic particle size analyzer that uses two charging chambers rather than one. In this particular embodiment, the electrodes are circular arid the enclosure is cylindrical.

As shown in FIG. 4A this embodiment comprises a circular base plate 72 on which is removably attached a pressure lid 74 forming an enclosure 73. An "o" ring 76 may be used to provide hermetic sealing of the enclosure. The sealed enclosure may then be pressurized in excess of atmospheric pressures by the introduction of a gas from a source 71 of high-pressure gas. The details of the gas source are not shown, but may comprise any apparatus conventionally known for supplying a gas under pressure to an enclosure.

Introducing high-pressure gas into the embodiment herein described presents certain advantages. As can be seen from FIG. 2, increasing the electric field intensity increases the terminal velocity sensitivity to particle radius. Similarly, equation 1 shows that charge is directly proportional to electric field intensity. Thus, for decreasing particle sizes, the accuracy of the particle size determination can be enhanced through the use of increasing field strengths. However, because electric field intensity is defined as the potential difference between the electrodes divided by the distance between them, either increased electrode voltages or decreased electrode spacing is necessary to generate increased electric fields, thus increasing the risk of arc generation between the electrodes. Increasing the gas pressure increases the dielectric strength of the gas and thus reduces arcing potential, as the conductivity of a gas is inversely proportional to its pressure. Thus, the ability to operate the present invention at higher pressures enables use of higher voltage fields, and thereby extends the measurement range for accurate determination of smaller particles sizes.

Within the enclosure 73 there is mounted on a ring-shaped support 93 a cylindrical particle-charging chamber 78. Charging chamber 78 has a circular bottom electrode 86 and a circular top electrode 90 supported on insulating ring spacers 82 and 84, which in turn are mounted on a non-conducting ring wall 80.

The top electrode 90 is mounted on the underside of a cover 92 that is removably mounted on the ring wall 80.

Also supported by the spacers 82 and 84 is a middle electrode 88. Middle electrode 88 is located between top electrode 90 and bottom electrode 86 and is spaced therefrom. Middle electrode 88 divides the chamber into a first, upper section and a second, lower section.

The middle electrode is preferably piano-concave upward with its apex opposite the top electrode and convex downward with the apex opposite the exit orifice. It contains an orifice 89 placed away from the apex. An off-center orifice in the middle electrode allows powder to flow from the upper chamber section to the lower chamber section. Bottom electrode 86 also contains an orifice 87 that is preferably located at the center of the circular electrode. There can be a plurality of middle electrodes creating a plurality of chambers. Increasing the number of chambers dilutes the concentration of particles in the each successive chamber, thus reducing the probability of multiple particles simultaneously exiting the bottom orifice of the bottom electrode. The size of the orifice hole may also be instrumental in minimizing the escape of multiple particles from each chamber. For example, for an electrode having a diameter of 110 to 120 mm intended for measuring particles in the 10 to 500 micron range, the orifice may have a diameter in the range of 2 to 3 mm. The electrode size and corresponding orifice size, however, may be tailored to the specific application, with relatively smaller sized orifices being used in applications for measuring relatively smaller sized particles.

Co-axial with the electrodes and particle-charging chamber, and below the chamber, is the collector electrode 102. The collector electrode is made of highly conductive materials, preferably shaped as a cylinder 104 having an open top and a closed bottom 106 in the shape of a cone with the pointed end extending into the interior of the cylindrical electrode. This shape is preferred because it corrects for the abnormalities in the electric field caused by the orifice in the bottom electrode. Without this shape of the collecting electrode, particles leaving the bottom electrode orifice can stick to the underside of the bottom electrode and are more likely to make multiple bounces on the collector electrode. Dielectric insert 100 in the base plate 72 supports the collector electrode. An electrical contact 108 extends from the collector electrode 102 through the insert 100 to outside the enclosure 73.

Figure 4B:
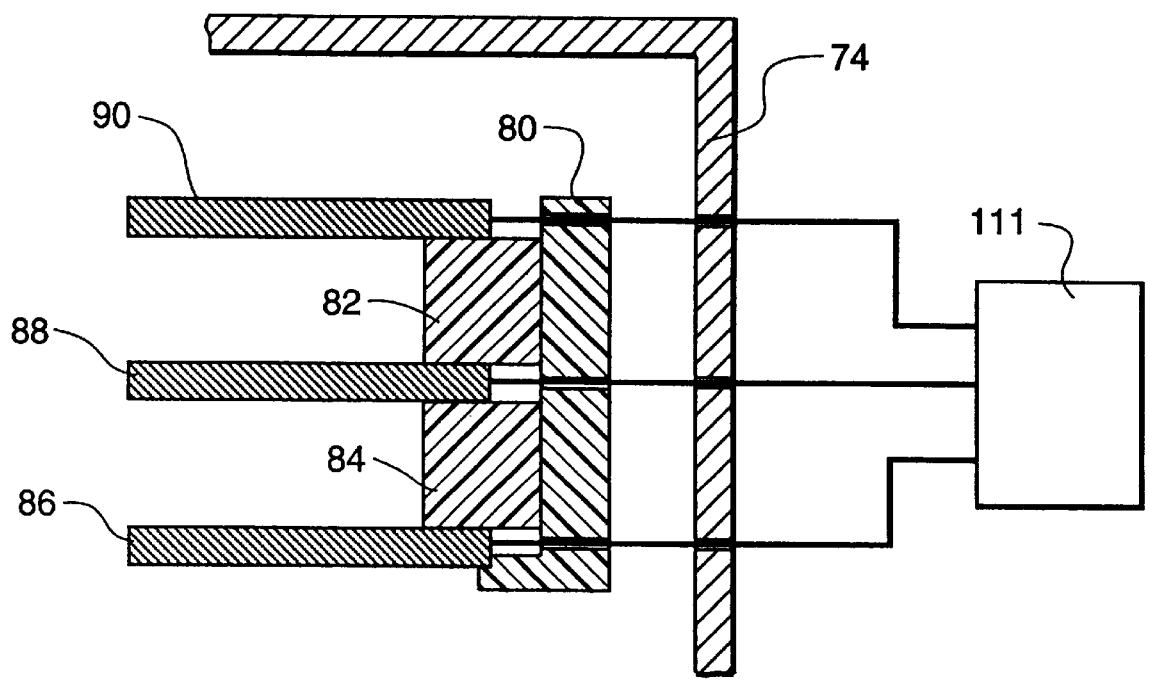
FIG. 4B shows a magnified schematic illustration of the electrode spacing in the alternate embodiment of FIG. 4A.

Not illustrated in FIG. 4A are additional electrical connections extending from the top, middle and bottom electrodes to outside the enclosure 73 for connecting thereto a source of DC voltage that is used to charge the sample of particles to be measured. This charging arrangement is schematically shown in FIG. 4B in which power supply 110 is connected to electrodes 90, 88, and 86. In a typical such arrangement the charging voltage is such that middle electrode 88 is positively charged with respect to bottom electrode 86 and negatively charged with respect to top electrode 90. The charging voltage must be kept below the magnitude that will produce arcing in the presence of particles between the electrodes. An alternate embodiment may have multiple middle electrodes, in which case the voltage between the top electrode and topmost middle electrode, between each pair of successive middle electrodes, and between the lowermost middle electrode and the bottom electrode must all be insufficient to produce arcing. Where a vacuum tube electrometer is used for measurement of particle charge, middle electrode 88 (or lowermost middle electrode in a multiple-riddle-electrode embodiment) is negatively charged to provide a negative particle charge.

In apparatus of this type where the electrode spacing is of the order of 3–5 mm, and the gas in the chamber is nitrogen of a controlled relative humidity at 10 atmospheres, the voltage differential between the bottom and middle electrodes may be on the order of 10 Kilovolts (kV), and the voltage between the middle electrode and the top electrode may be on the order of 10 kV. Voltage between the bottom and the collector is typically 0.8 kV to 3 kV.

Many variations of the voltages are possible. Such variations are easily achieved by adjusting the voltage supplies to the electrodes, some of which may offer superior performance under certain circumstances, and all of which are anticipated by the present invention. These adjustments can be made under manual or computer control.

Referring next to both FIGS. 4 and 5 there is shown a preferred arrangement for determining the velocity of particles exiting the charging chamber 78 through orifice 87 and traveling toward the collecting electrode 102.

The cylindrical support ring 93 has an inside surface that is a polished dielectric mirror surface 94. Within support ring 93 there are placed two light bending prisms, an entry prism 96 and an exit prism 97. The prisms are mounted on the base 72 and permit light to enter and exit the enclosure 73.

A light source 95, preferably a laser light source is located so that light emitted from the light source enters the enclosure through prism 96 in the space inside support 93 and beneath the bottom electrode. As shown in FIG. 5, the beam is split into at least two (or more) parallel and coplanar fanned beams 110 and 112 that pass under the orifice 87. As shown in FIG. 5, inside the enclosure 73, each of the laser beams 110, 112 is shaped as a thin fan which completely covers the area below the orifice 87. A light trap 114 is placed across from the entering light beams to intercept the beams and prevent light from being reflected from polished inner surface 94 of the cylindrical support 93.

Prism 97 is placed outside the direct path of the light beams 110 and 112. Preferably, the polished inner surface 94 is shaped so as to direct any light incident thereon to exit prism 97. A light detector, such as a photodiode 98 is placed so as to receive light through the prism 97 and generate an electrical signal.

In operation, lid 74 of enclosure 73 is opened, and a small quantity of dry particles, generally in the range of 0.1 $\mu$m–1000 $\mu$m, is placed in the charging chamber 78. Where there is a middle electrode present as shown in FIG. 4A, the particle sample is placed in the top portion of the charging chamber on middle electrode 88. (In a two-electrode apparatus such as that shown in FIG. 1A, it is placed on the bottom electrode 18.)

The lid 73 is then replaced on base plate 72 and secured thereto. Preferably the enclosure is next filled with a gas, in particular an inert gas such as nitrogen having a controlled humidity greater than zero, and brought to a pressure above atmospheric, such as 10 atmospheres. The gas cannot be completely dry, because a surface layer of water adsorbed to dielectric particles is needed for charging them.

A high voltage is then applied to the electrodes 86, 88, and 90, thus pseudo-fluidizing the particles and causing them to oscillate between electrodes. As used herein, "pseudo-fluidizing" means making the particles behave as a fluid; thus, a "pseudo-fluidization chamber" as used herein defines a chamber capable of imparting fluid behavior on the particles. Eventually charged particles exit the charging chamber 78 through orifice 87 and pass through the laser beam fans 110 and 112. As each particle 24" enters the laser beam fan, it scatters light, as is shown by the dotted lines 109 in FIG. 3. The scattered laser light is reflected by dielectric mirror surface 94 and is collected by exiting prism 97. The photodiode detector connected to the prism produces a pulse. As the second beam is traversed, a second pulse is produced. The known distance divided by the time difference between the two pulses provides the particle velocity. Where only a single laser beam fan is present, the particle velocity is computed by dividing the known distance between the single beam and the collector electrode by the time difference between the pulse generated when the particle passes through the single beam and the pulse generated when the particle hits the collector electrode (discussed below).

After passing through the laser beam fan or fans, the particles impinge on the collector electrode 106, generating an electrical pulse having an integral proportional to the charge on the particle. These pulses are individually collected and the pulse magnitudes stored in a memory. A histogram of the frequency of the magnitudes is constructed to provide a measure of the charge distribution detected. Because the charge is related to the particle surface area the histogram also represents a surface area distribution of the particles in the sample. Other means for representing the charge distribution and/or surface area distribution may also be generated in addition to or in place of a histogram.

To provide an accurate determination of the relationship between measured charge and surface area, the method for determining particle size distribution may first comprise developing a calibration curve for a plurality of calibration particles having a known particle size distribution.

The calibration curve can be developed by first introducing the calibration particles in charging chamber 78 and applying charge to the electrodes 86, 88, and 90. The charged calibration particles exit through bottom electrode orifice 87 and are collecting in collecting electrode 102. The calibration particles generate electrical signals having magnitudes indicative of their charge as they hit collecting electrode 102, and those electrical signal magnitudes are stored.

Next, a plurality of sample particles having an unknown particle size distribution are introduced into charging chamber 78 and charge is applied to the electrodes 86, 88, and 90. The charged sample particles exit through bottom electrode orifice 87 and are collected in collecting electrode 102. The electrical signals generated by the sample particles hitting collecting electrode 102 are compared to the similar stored signals obtained from the calibration particles to obtain a signal indicative of the actual sample particle size distribution.

A calibration run may be performed with the apparatus at occasional intervals to make adjustments to the electronics and computational constants as necessary to assure that the calibration sample produces the expected results.

Once the surface area is determined, the actual size and shape of the particles may be estimated by making certain assumptions. For instance by assuming that the particles are spherical, the estimated diameter of the particles may be derived and thus the estimated particle volume distribution may also be derived. The volume distribution may also be derived if the particles have a known non-spherical shape. If the particles have a known shape and a known density, the particle mass distribution may be calculated. The measured terminal velocity may also be incorporated into the volume and mass determinations.

As previously detailed, particle velocity is determined by measuring the time of flight of a particle between successive light beams of known spacing or between a single light beam and the collector electrode having a known spacing. If more than two light beams are provided, an improved estimate of the velocity can be obtained, including the ability to verify that a particle has reached terminal (i.e. steady state) velocity. Better discrimination of multiple particles is also possible because a higher number of beams decreases the probability that simultaneous particles cross all the beam paths at the same time and are counted as a single particle. It is advantageous to use the real-time computed velocity of the particles to form a timing window for pulse acquisition/noise discrimination in order to improve the signal to noise ratio. The differing statistics of the noise and the pulses can be advantageously used to discriminate between the pulse information and the noise.

The velocity of each particle can also be compared to the predicted terminal velocity of a particle having a known shape and an area measured by the charge detection element of the apparatus. Any difference between predicted and actual terminal velocity can be correlated to anomalous drag on the particle. Anomalous drag is influenced by the deviation of the particle from a spherical shape, and thus the particle speed in conjunction with its charge can be used to deduce information about the particle shape. This is especially useful where the apparatus is used for product quality control and is calibrated with particles having a known desired particle shape, and where deviation in shape indicates off-specification product.

Although described herein with reference to a preferred embodiment wherein the particle charging chamber comprises a chamber for electrodynamic charging and pseudo-fluidization of particles, other particle charging chambers employing other methods of charging and/or pseudo-fluidization may also be used with the remaining elements of the invention. What is important, however, is that the particle charging chamber provides particles charged in proportion to some dimension of the particle, such as surface area or volume, and that the particle charging chamber is capable of releasing the particles from the chamber primarily one at a time. "Primarily one-at-a-time" means that, for example as described with respect to the electrodynamic particle charging chamber detailed herein, that most of the time the particles discharge only one-at-a-time. Even with electrodynamic particle charging and pseudo-fluidization with an appropriately sized exit orifice on the bottom electrode, however, it randomly and occasionally occurs that multiple particles leave through the exit orifice simultaneously. Thus, it is also beneficial to be able to discriminate between single and multiple particles, such as described above with respect to the fan-shaped light beams.

Those having the benefit of the above disclosure will recognize that a number of modifications may be made without departing from the main concept described hereinabove. All such modifications are to be construed as been encompassed by the invention as set forth in the appended claims.

What is claimed is:

1. An apparatus for determining the particle size distribution of a plurality of particles in a sample comprising:
   a particle charging chamber having an exit passage, said charging chamber adapted to charge said particles to a saturation level proportional to a dimension of the particle and to release the charge-saturated particles through the exit passage primarily one-at-a-time;
   a collector electrode located outside said particle charging chamber and aligned with the exit passage and spaced therefrom;
   a charge-measuring device connected to said collector electrode, said charge-measuring device adapted to provide an output signal representative of measured particle charges.

2. The apparatus of claim 1 wherein the dimension of the particle proportional to which the particle charging chamber is adapted to charge the particles comprises one of: surface area or volume.

3. The apparatus of claim 1 wherein the particle charging chamber is further adapted to pseudo-fluidize said particles.

4. The apparatus of claim 1 wherein the particle charging chamber comprises an electrodynamic pseudo-fluidization chamber.

5. The apparatus of claim 4 wherein the particle charging chamber further comprises:
   a top electrode;
   a bottom electrode spaced from said top electrode and having an inner surface facing said top electrode and an outer surface opposite said inner surface;
   an insulating side wall extending between said top and bottom electrodes;
   an exit orifice in said bottom electrode that comprises the exit passage from the particle charging chamber; and
   means for inserting said plurality of particles in said chamber;
   and said apparatus further comprises a DC voltage source connected between said top and bottom electrodes for applying a first voltage to said electrodes, the first voltage having a magnitude which is insufficient to cause arcing between said top and bottom electrodes.

6. The apparatus according to claim 5 wherein the collector electrode has a potential that is adjustable relative to the bottom electrode.

7. The apparatus of claim 5 wherein said charge-measuring device is a vacuum tube electrometer and said top electrode has a negative charge.

8. The apparatus according to claim 5 wherein the top and bottom electrodes are coplanar and coextensive disks and wherein the orifice is located at the center of the bottom electrode.

9. The apparatus of claim 5 wherein the collector electrode has a hollow cylindrical shape having an open top facing said bottom electrode and a closed bottom opposite said open top.

10. The apparatus of claim 9 wherein the collector electrode bottom has a conical shape with a pointed end extending axially toward the open top of the cylindrical collector electrode.

11. The apparatus according to claim 5 wherein the particle charging chamber further comprises:
    one or more middle electrodes located in said chamber between said top and said bottom electrodes and spaced therefrom, each middle electrode having an exit orifice; and
    wherein the DC voltage source is adapted to apply a DC voltage between each pair of adjacent electrodes insufficient to generate arcing between the adjacent electrodes.

12. The apparatus according to claim 11 wherein the particle charging chamber comprises one middle electrode, and the DC voltage source is adapted to apply a first DC voltage between the middle electrode and the bottom electrode and a second DC voltage between the top electrode and the middle electrode.

13. The apparatus according to claim 12 wherein the middle electrode has a surface facing the top electrode and said surface is a convex surface having an apex, and wherein the middle electrode exit orifice is placed away from the apex of the convex surface.

14. The apparatus according to claim 12 wherein said charge-measuring device is a tube electrometer and said middle electrode has a negative charge.

15. The apparatus of claim 1 further comprising:
    a display adapted to provide a readout correlated to said output signal.

16. The apparatus of claim 1 further comprising a conversion device adapted to receive the output signal from said charge measuring device and to convert said output signal representative of measured particle charges to a particle surface area distribution.

17. The apparatus of claim 16 wherein said particles have a known shape, and said conversion device is further capable of converting said known shape and said particle surface area distribution into a particle volume distribution.

18. The apparatus of claim 16 wherein said particles have a known shape and density, and said conversion device is further capable of converting said known shape and density and said particle surface area distribution into a particle mass distribution.

19. The apparatus of claim 1 further comprising an enclosure defining a space enclosing the particle charging chamber and collector electrode.

20. The apparatus of claim 19 wherein the space within the enclosure contains gas above atmospheric pressure having a controlled relative humidity.

21. The apparatus of claim 20 wherein said gas comprises an inert gas.

22. The apparatus according to claim 1 further comprising means for discriminating the presence of multiple particles released essentially simultaneously through the particle charging chamber exit passage.

23. The apparatus according to claim 1 further comprising:
    one or more fan-shaped light beams defining a plane between the particle charging chamber exit passage and the collector electrode, and
    a means for detecting any beam disruption by the passage of a charged particle and for generating an electrical signal indicating the passage of any such particle through each of said light beams.

24. The apparatus according to claim 23 further including:
    a timer adapted to measure a time of flight of an individual particle between (a) the electrical signal indicating passage of the individual particle through a first of said fan-shaped light beams and (b) one of: the electrical signal indicating passage of the individual particle through another of said fan-shaped light beams, or an electrical signal indicating collision of the individual particle with the collector electrode.

25. The apparatus of claim 24 wherein said conversion device is further capable of converting said time of flight and said measured particle charge into a calculated particle mass.

26. The apparatus according to claim 24 further including:
at least two said fan-shaped light beams in parallel spaced planes between the particle charging chamber exit passage and the collector electrode.

27. A method for determining a particle size distribution of a plurality of particles having a plurality of sizes by charging said plurality of particles and measuring a charge magnitude for each particle, the method comprising the steps of:
   a) charging each of said particles to a saturation level proportional to a particle dimension in a particle charging chamber having an exit passage that releases said charge-saturated particles from the charging chamber primarily one particle at a time;
   b) collecting any charged particles exiting the particle charging chamber through said exit passage and generating an electrical signal having a magnitude indicative of the charge of any such escaping charged particle; and
   c) using a distribution of the electrical signal magnitudes of a plurality of charged particles as an indicator of the particle size distribution.

28. The method of claim 27 wherein step (a) further comprises pseudo-fluidizing said particles in said particle charging chamber.

29. The method of claim 27 wherein each particle has a surface area, wherein step (a) comprises charging each of said particles to the saturation level proportional to the particle surface area, and step (c) comprises using the distribution of the electrical signal magnitudes as an indicator of the particle surface area distribution.

30. The method of claim 27 wherein the particle charging chamber comprises a first pair of electrodes having a first space therebetween, one of the electrodes having an orifice, and step (a) comprises introducing the plurality of particles in the first space between the first pair of electrodes in the presence of a static electric field.

31. A method for determining the particle size distribution in a sample containing a plurality of different size particles, the method comprising the steps of:
   a) establishing an electric field in a space between two electrodes;
   b) introducing the particles in said space;
   c) causing a charge to accumulate on said particles, said charge being proportional to the surface area of the particles, whereby said particles begin to oscillate between said electrodes under the influence of the electric field;
   d) allowing said charged particles to escape the space between said electrodes;
   e) capturing the escaping particles one at a time; and
   f) measuring the charge magnitude on each of the captured escaping particles.

32. A method for determining the particle size distribution in a sample containing a plurality of different size particles, the method comprising the steps of:
   a) establishing an electric field in a space between two electrodes;
   b) introducing the particles in said space;
   c) causing a charge to accumulate on said particles, said charge being proportional to the surface area of the particles, whereby said particles begin to oscillate between said electrodes under the influence of the electric field;
   d) allowing said charged particles to escape the space between said electrodes;
   e) capturing the escaping particles;
   f) measuring the charge magnitude of the captured escaping particles; and
   g) determining the frequency of occurrence of different measured charge magnitudes and correlating the measured charge magnitude to the surface area of the particles carrying the measured charges.

33. The method according to claim 32 wherein step (g) further comprises providing an output comprising a representation of the frequency of occurrence of different measured charge magnitudes as correlated to the surface area of the particles carrying the measured charges.

34. The method according to claim 33 wherein providing the output in step (g) further comprises providing a histogram of the frequency of occurrence of different measured charge magnitudes as correlated to the surface area of the particles carrying the measured charges.

35. A method for determining the particle size distribution in a sample containing a plurality of different size particles, the method comprising the steps of:
   a) establishing an electric field in a space between two electrodes;
   b) introducing the particles in said space;
   c) causing a charge to accumulate on said particles, said charge being proportional to the surface area of the particles, whereby said particles begin to oscillate between said electrodes under the influence of the electric field;
   d) allowing said charged particles to escape the space between said electrodes;
   e) capturing the escaping particles; and
   f) measuring the charge magnitude of the captured escaping particles;
   further comprising between steps (d) and (e) a step of measuring a terminal velocity of the escaping charged particles and discriminating the presence of multiple particles.

36. The method according to claim 35 wherein the process further comprises:
   h) correlating the measurement of the charge magnitude and the terminal velocity of the escaping charged particles to derive a particle mass distribution of the sample.

37. A method for determining the particle size distribution in a sample containing a plurality of different size particles comprising the steps of:
   a) developing a calibration curve showing a surface charge distribution for a plurality of calibration particles having a known particle size distribution, by
      1) charging each of said calibration particles by introducing said plurality of calibration particles in a space between a pair of electrodes, one of said electrodes having an orifice, in the presence of a static electric field;
      2) collecting any charged calibration particles exiting said space through said orifice in said electrode and generating an electrical signal having a magnitude indicative of the charge of any such escaping charged calibration particle; and
      3) storing the distribution of the electrical signal magnitudes of a plurality of charged calibration particles;
   b) charging a plurality of sample particles having an unknown particle size distribution by 1) charging each of said sample particles by introducing said plurality of sample particles in said space between said pair of electrodes in the presence of said static electric field;
2) collecting any charged sample particles exiting said space through said orifice in said electrode and generating an electrical signal having a magnitude indicative of the charge of any such escaping charged sample particle; and
3) comparing the electrical signal generated in step b(2) with the stored signal obtained in step a(4) to obtain a signal indicative of the actual sample particle size distribution.

* * * * *